US009846026B2

(12) United States Patent
Haverkamp

(10) Patent No.: US 9,846,026 B2

(45) Date of Patent: Dec. 19, 2017

(54) LIGHT-EMITTING TABLE SUITABLE FOR USE IN METROLOGY, AND COORDINATE MEASURING MACHINE HAVING SUCH A LIGHT-EMITTING TABLE

(71) Applicant: Carl Zeiss Industrielle Messtechnik GmbH, Oberkochen (DE)

(72) Inventor: Nils Haverkamp, Aalen (DE)

(73) Assignee: Carl Zeiss Industrielle Messtechnik GmbH, Oberkochen (DE)

( * ) Notice: Subject to any disclaimer, the term of this patent is extended or adjusted under 35 U.S.C. 154(b) by 0 days.

(21) Appl. No.: 15/277,254

(22) Filed: Sep. 27, 2016

(65) Prior Publication Data

US 2017/0016713 A1 Jan. 19, 2017

Related U.S. Application Data

(63) Continuation of application No. PCT/EP2015/055658, filed on Mar. 18, 2015.

(30) Foreign Application Priority Data

Mar. 27, 2014 (DE) ........................ 10 2014 205 705

(51) Int. Cl.
*G01B 11/00* (2006.01)
*G02B 19/00* (2006.01)
(Continued)

(52) U.S. Cl.
CPC .......... *G01B 11/005* (2013.01); *G01B 5/0007* (2013.01); *G01B 11/2433* (2013.01);
(Continued)

(58) Field of Classification Search
CPC G01B 11/005; G01B 5/0007; G01B 11/2433; G02B 5/205; G02B 19/0019; G02B 19/0028
See application file for complete search history.

(56) References Cited

U.S. PATENT DOCUMENTS 5,327,195 A 7/1994 Ehr
5,347,342 A 9/1994 Ehr
(Continued)

FOREIGN PATENT DOCUMENTS

DE 44 42 787 C1 6/1996
DE 200 17 739 U1 1/2001
(Continued)

OTHER PUBLICATIONS

Written Opinion of the International Searching Authority dated Aug. 5, 2016 of international application PCT/EP2015/055658 on which this application is based.

(Continued)

*Primary Examiner* — Kara E Geisel
*Assistant Examiner* — Rebecca C Bryant
(74) *Attorney, Agent, or Firm* — Walter Ottesen, P.A.

(57) ABSTRACT

A light-emitting table suitable for use in metrology includes a plurality of light sources and a field to be illuminated. Light-emitting centers of the light sources represent starting points of light source axes which perpendicularly intersect the field to be illuminated. The light-emitting centers of the light sources on one side and the field to be illuminated on the other side delimit an intermediate space in the interior of the light-emitting table. Located between the light source axes within the intermediate space are curved and mirrored surfaces, the focal points or caustics (K) of which are located within the intermediate space between the curved and mirrored surfaces and the field to be illuminated. A coordinate measuring machine for capturing the coordinates of a workpiece includes at least one optical sensor and a light-emitting table for illuminating the workpiece during measurement of the coordinates of the workpiece using the sensor.

14 Claims, 10 Drawing Sheets

(51) Int. Cl.

| | |
|---|---|
| ***G01B 5/00*** | (2006.01) |
| ***G01B 11/24*** | (2006.01) |
| ***G02B 27/09*** | (2006.01) |
| ***G02B 5/20*** | (2006.01) |
| *G01N 21/88* | (2006.01) |

(52) U.S. Cl.

CPC ......... *G02B 5/205* (2013.01); *G02B 19/0019* (2013.01); *G02B 19/0028* (2013.01); *G02B 19/0061* (2013.01); *G02B 19/0066* (2013.01); *G02B 27/0927* (2013.01); *G01N 2021/8816* (2013.01)

(56) References Cited

U.S. PATENT DOCUMENTS

| | | | |
|---|---|---|---|
| 6,161,940 A | 12/2000 | Choate et al. | |
| 6,323,953 B1 | 11/2001 | Blaesing-Bangert et al. | |
| 7,268,867 B2 | 9/2007 | Vollrath et al. | |
| 8,562,802 B1 | 10/2013 | Beaudet et al. | |
| 9,316,378 B2 | 4/2016 | Ebner | |
| 2003/0202241 A1 | 10/2003 | Blumel | |
| 2004/0080938 A1* | 4/2004 | Holman | F21S 8/08 362/231 |
| 2005/0190559 A1 | 9/2005 | Kragl | |
| 2006/0030026 A1 | 2/2006 | Garcia | |
| 2006/0104060 A1 | 5/2006 | Kragl | |
| 2006/0237658 A1 | 10/2006 | Waluszko | |
| 2007/0069643 A1 | 3/2007 | Brunner et al. | |
| 2008/0308752 A1 | 12/2008 | Park | |
| 2015/0036114 A1 | 2/2015 | Schadt et al. | |

FOREIGN PATENT DOCUMENTS

| | | |
|---|---|---|
| DE | 103 08 917 A1 | 9/2004 |
| DE | 10 2011 078 287 A1 | 1/2013 |
| JP | 2009-176488 A | 8/2009 |
| WO | 2013/010718 A1 | 1/2013 |

OTHER PUBLICATIONS

International Search Report dated Jun. 5, 2015 of international application PCT/EP2015/055658 on which this application is based.

Partial English translation and Office action of the German Patent Office dated Jan. 12, 2015 in German patent application 10 2014 205 705.1 on which the claim of priority is based.

* cited by examiner

LIGHT-EMITTING TABLE SUITABLE FOR USE IN METROLOGY, AND COORDINATE MEASURING MACHINE HAVING SUCH A LIGHT-EMITTING TABLE

CROSS REFERENCE TO RELATED APPLICATIONS

This application is a continuation application of international patent application PCT/EP2015/055658, filed Mar. 18, 2015, designating the United States and claiming priority from German application 10 2014 205 705.1, filed Mar. 27, 2014, and the entire content of both applications is incorporated herein by reference.

FIELD OF THE INVENTION

The invention relates to a light-emitting table for use in metrology, and to a coordinate measuring machine including such a light-emitting table.

BACKGROUND OF THE INVENTION

Light-emitting tables for various uses are known, for example, from U.S. Pat. Nos. 5,327,195 and 5,347,342, United States patent application publications 2006/0030026, 2006/0237658, 2007/0069643 and 2008/0308752 and U.S. Pat. No. 8,562,802. United States patent application publication 2006/0030026 discloses that LED light sources for collimating the light emitted by the light sources can be fitted with lens elements. In contrast, in United States patent application publications 2007/069643 and 2006/0237658, without any collimation, only the far field that is homogeneously illuminated by a grid of LED light sources is used as a field for the light-emitting tables, which results in a large installation space for the light-emitting tables.

Moreover, United States patent applications 2006/0104060 and 2005/0190559 disclose the provision of individual LED light sources with a parabolic mirror for collimation of the LED light. Here, the center of the surface of the light-emitting diode chip is located in the focal point or focal line of the parabolic mirror. Laid-open specification DE 103 08 917 A1 furthermore discloses the provision of an LED chip with a conical, spherical or parabolic reflector for collimating the LED light. However, all the stated reflectors for LED light sources are distinguished by the fact that they have a focal point or a caustic for normal incidence of light from infinity and that the optically active surface of the LED chip is located in exactly this focal point or within this caustic.

In the above-mentioned light-emitting tables of the prior art, be it with LED light sources or not, be it with the use of reflector technology for collimation or not, optically diffusing elements, such as for example diffusing plates or diffusing films, are generally used to homogenize the intensity distribution over the light-emitting table field that is to be illuminated. The goal is here generally to limit the homogeneity of the light-emitting table field, that is, the variation of the illumination intensity over the field with respect to the average illumination intensity of the field, to less than 5%. However, this good homogeneity of prior art light-emitting tables is generally achieved by statistically diffusing optical elements, as a result of which the light-emitting table field emits light diffusely in virtually every direction of the half-space located thereabove. However, this broad illumination angle distribution of light-emitting tables of the prior art is unsuitable for many measurement types of coordinates of a workpiece using optical sensors by way of a coordinate measuring machine, in particular for measurements of edges or holes. Consequently, the cost-effective light-emitting tables of the prior art are generally not used, or used only to a very limited extent, for use in metrology.

By contrast, coordinate measuring machines for measuring coordinates of a workpiece to be measured using an optical sensor utilizing what is known as transmitted-light illumination using a complicated illumination optics are known, for example, from U.S. Pat. No. 6,161,940.

Generally, an attempt is made in such coordinate measuring machines for the purpose of increasing resolution to select what is known as the opening angle of the lens used for viewing the workpiece such that it is as large as possible. Accordingly, an associated condenser optics for illuminating the workpiece must provide a tuned maximum illumination angle at the light-emitting table field. Moreover, an attempt is frequently made in these coordinate measuring machines using a variable condenser optics to provide the optimum illumination of the workpiece for the structures to be measured in each case and lens settings. This variability of the condenser optics, however, is at the same time accompanied by a certain complexity in terms of the construction of the condenser optics, which is also associated with correspondingly high costs for producing such a condenser optics.

However, this complicated method of illumination-angle setting in coordinate measuring technology also encounters its limits when it comes to measuring structures having a large extent along the optical axis, since the depth of field decreases as the opening angle increases, and thus structures having a large distance from the light-emitting table field are imaged "without sharpness." For measuring structures having a large extent along the optical axis perpendicular to the light-emitting table field, such as for example the planes of edges, it therefore makes sense if the illumination light at the light-emitting table field is aligned to be parallel and thus collimated with respect to the optical axis. In this case, structures having a large distance from the light-emitting table field can be measured at the same accuracy as structures having a small distance from the light-emitting table field. In addition, these structures can also be measured in relation to one another, as long as a telecentric lens is used for imaging onto the optical sensor.

SUMMARY OF THE INVENTION

It is therefore an object of the invention to provide a simple and cost-effective light-emitting table for metrological use and a corresponding coordinate measuring machine having such a light-emitting table which permits illumination light that is aligned so as to be in particular collimated, that is, nearly parallel, for measuring edges of and holes in a workpiece.

This object is, for example, achieved by way of a light-emitting table that is suitable for use in metrology. The light-emitting table includes a plurality of light sources and a field to be illuminated. The light-emitting centers of the light sources represent the starting points of light source axes which perpendicularly intersect the field to be illuminated. The light-emitting centers of the light sources on one side and the field to be illuminated on the other side delimit an intermediate space in the interior of the light-emitting table. Curved and mirrored surfaces are located between the light source axes within the intermediate space. The focal points or caustics of the curved and mirrored surfaces are located within the intermediate space between the curved and mirrored surfaces and the field to be illuminated.

Owing to the use of these curved and mirrored surfaces between the light source axes, which, due to the stated position of the focal points or caustics, are aligned with the field to be illuminated, it is possible to fill the otherwise unused shadow region between the light sources with illumination light and at the same time maintain the collimation of the illumination light. Owing to these curved and mirrored surfaces it is thus possible both to improve the homogeneity of the light-emitting table and to ensure collimation of the illumination light. To this end, the curved and mirrored surfaces have surface shapes, the local curvatures of which are configured such that visible light that is incident on the field of the light-emitting table parallel to the light source axes and counter to the illumination direction of the light-emitting table collects, owing to the curved and mirrored surfaces, in focal points or caustics above the light sources and above the curved and mirrored surfaces in the intermediate space between the light sources and the field of the light-emitting table. In other words, neither the light sources nor the light-emitting centers of the light sources are located in the focal points or within the caustics of the curved and mirrored surfaces of the light-emitting table according to the invention viewed under normal incidence of light on the light-emitting table field from infinity. The surface shape of the curved and mirrored surfaces can vary strongly here depending on the overall configuration of all optically effective surfaces of the light-emitting table, from spherical to aspherical, rotation-symmetrical and non-rotation-symmetrical up to the surface shape of what are known as freeform optics.

In one embodiment of the light-emitting table, the light sources are arranged parallel in a regular first pattern having spacings of 0.2 cm to 4 cm, and the curved and mirrored surfaces are arranged in a second pattern, corresponding to the first pattern, with a lateral offset to the light sources or to the light source axes, with the result that next to the curved and mirrored surfaces, free regions through which illumination light is able to pass are located around the light source axes. This type of construction of the light-emitting table permits the illumination light from the light sources to be incident on the field of the light-emitting table without considerable losses along first, so-called primary light channels and to cause here illumination of the field.

In a further embodiment of the light-emitting table, primary light channels of the light-emitting table, starting from the light sources, along the light source axes, are present, the extent of which in a plane perpendicular to the optical light source axes is given by the passable free regions, and wherein located in the primary light channels of the light-emitting table are light-deflecting and/or light-refracting and/or light-diffracting means, which align the illumination light within the primary light channel parallel to the light source axis with a parallelism of better than 2°, and wherein the means are formed by the group: curved mirrors, parabolic mirrors, hyperboloidal mirrors, ellipsoidal mirrors, lens elements, Fresnel lens elements, cylindrical lens elements, microlens elements, honeycomb condensers, diffractive optical elements. The collimation means make it possible for the illumination light from the light sources to be aligned parallel in the primary light channels. As a result, the illumination light is incident on the field of the light-emitting table from a nearly normal direction. As a result, a larger variation of illumination angles at the field points of the light-emitting table within the primary light channels is avoided, especially since the use of diffusing optical elements for homogenization in the primary light channels is entirely dispensed with.

In one embodiment of the light-emitting table, located in the primary light channels of the light-emitting table, which are defined by the free regions around the light source axes, between the curved and mirrored surfaces and the field of the light-emitting table, are further curved and partially mirrored surfaces which reflect a proportion of illumination light out of the primary light channels toward the curved and mirrored surfaces at angles of up to 50° with respect to the light source axes. Owing to these further curved and partially mirrored surfaces within the primary light channels, a proportion of illumination light is coupled out of the primary light channels and used for supplying the secondary light channels which are formed or defined by the curved and mirrored surfaces next to the light source axes.

In a further embodiment of the light-emitting table, the light sources are provided by what are known as LEDs or OLEDs, and the local curvatures of the curved and mirrored surfaces and the local curvatures of the further curved and partially mirrored surfaces are configured with respect to one another such that illumination light, which travels within the primary light channels near the light source axis and is reflected by the surfaces, subsequently travels within the secondary light channels, which are defined by the curved and mirrored surfaces, remote from the light source axis, and vice versa.

What is achieved with this type of redistribution of illumination light in the secondary light channels is that light which previously traveled within the primary light channel near the light source axis travels, after it has been coupled out, in the respective secondary light channel remote from the light source axis. This type of redistribution makes sense in particular for homogenizing the field of light-emitting tables with LED or OLED light sources, since these light sources have an emission characteristic with which most of the light is emitted closely around the light source axis. In addition, this also counters the geometric effect that the surface regions of the secondary light channels, which are to be supplied with light, are, in terms of their surface area, a function of the square of the distance from the respective light source axis.

In one embodiment of the light-emitting table, the reflectivity properties along the partially mirrored surfaces are additionally configured such that higher reflectivity values of the partially mirrored surfaces are present around the light source axes than at the boundaries of the partially mirrored surfaces, with the result that proportionally more illumination light is reflected out of the primary light channels if this illumination light in the primary light channels travels near the light source axis before it is reflected out. This stated measure does not only serve for homogenizing the illumination light from LED or OLED light sources within the primary light channels of the light-emitting table by reducing here the illumination light in the primary light channels by way of increased outward reflection, where too much light for homogenization is already present anyway, but also for supplying most of the decoupled light to the boundaries of the secondary light channels.

In a further embodiment of the light-emitting table, the local curvatures of the curved and mirrored surfaces and also the local curvatures of the further curved and partially mirrored surfaces are configured with respect to one another such that the parallelism of the illumination light, which was originally achieved using the light-deflecting and/or light-refracting and/or light-diffracting means in the primary light channels, with respect to the light source axis of better than 2° is maintained in the further passage in the secondary light channels after the proportional outward reflection by way of the further curved and partially mirrored surfaces and the deflection by way of the curved and mirrored surfaces.

What is achieved as a result is that parallelism of the illumination light in the primary light channels, which is attained using the collimation means, is not destroyed again through outward reflection and deflection into the secondary light channels.

In one embodiment of the light-emitting table, the variation of the illumination intensity over the field of the light-emitting table is less than 3% of the average illumination intensity of the field, and the variation of the illumination angles at a point of the field is less than 2°, and the light-emitting table has a maximum installation height of 10 cm. It is thus possible to provide a light-emitting table for use in metrology, which can be used for measuring edges of and holes in a workpiece and is suitable for retrofitting of coordinate measuring machines owing to its low installation height.

In a further embodiment of the light-emitting table, the passable free regions around the light source axes are configured to be circular or elliptical, and the curved and mirrored surfaces represent contiguous, continuously differentiable surface regions, wherein the mentioned surface regions have honeycomb-type or circular or elliptical boundaries and are at least partially in contact with one another at the boundaries. As a result, optimum covering of the light-emitting table with secondary light channels is ensured.

In one embodiment of the light-emitting table, the curved and mirrored surfaces, which are in contact with one another, are formed on a unipartite carrier material using a pressing/thermoforming method and/or cold forming/hot forming and/or plastic injection molding, and the surface coating for making the curved and mirrored surfaces reflective is done using a method which includes at least one process step and/or one method step from the group: varnishing, vapor deposition, sputtering, separation from a chemical solution, grayscale lithography and subtractive methods for locally varying removal of a previously applied surface coating. Cost-effective production of the light-emitting table is made possible with the stated methods and process steps.

In a further embodiment of the light-emitting table, the unipartite carrier material likewise includes the light-deflecting and/or the light-refracting and/or the light-diffracting means of the light-emitting table, wherein the means are formed by plastic injection molding and/or a pressing/thermoforming method and/or cold forming/hot forming and/or by surface coating, wherein the surface coating includes at least one process step and/or at least one method step from the group: varnishing, vapor deposition, sputtering, separation from a chemical solution, grayscale lithography and subtractive methods for locally varying removal of a previously applied surface coating. As a result it becomes possible to form the collimation means on the unipartite carrier material in a cost-effective manner, rather than providing each light source individually and separately with its own collimation means.

In one embodiment of the light-emitting table, the further curved and partially mirrored surfaces are likewise formed on the unipartite carrier material by way of plastic injection molding and/or a pressing/thermoforming method and/or by cold forming/hot forming, wherein the surface coating for rendering the further curved and partially mirrored surfaces reflective is done using a method which includes at least one process step and/or one method step from the group: varnishing, vapor deposition, sputtering, separation from a chemical solution, grayscale lithography and subtractive methods for locally varying removal of a previously applied surface coating. As a result, all surfaces that are necessary for forming the primary and secondary light channels can be formed in the unipartite carrier material, as a result of which continuous production of the carrier material in the form of a film is made possible.

In a further embodiment, the light-emitting table has an ND filter for reducing the variation of the illumination intensity over the field to be illuminated. With such a neutral density filter (ND filter) it is possible to eliminate any remaining residual inhomogeneity in the illumination intensity distribution over the field of the light-emitting table.

In one embodiment, the light-emitting table has an ND filter, wherein the ND filter is formed on the unipartite carrier material and produced by way of surface coating, wherein the surface coating includes at least one process step and/or one method step from the group: varnishing, vapor deposition, sputtering, separation from a chemical solution, grayscale lithography and subtractive methods for locally varying removal of a previously applied surface coating. As a result, it is possible to implement cost-effective production of the ND filter.

In a further embodiment of the light-emitting table, the unipartite carrier material is assembled from at least two layers of different material having different optical densities, and the layers have locally varying, different geometric thicknesses along the lateral extent of the carrier material perpendicular to the light source axes. By using at least two layers of different material having different optical densities with locally varying, different geometric thicknesses, it is possible to introduce light-refracting optical elements into the unipartite carrier material in a cost-effective manner.

Moreover, the object is achieved by way of a coordinate measuring machine for capturing the coordinates of a workpiece, including at least one optical sensor and a light-emitting table according to the invention for illuminating the workpiece during a measurement of the coordinates of the workpiece using the at least one optical sensor.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
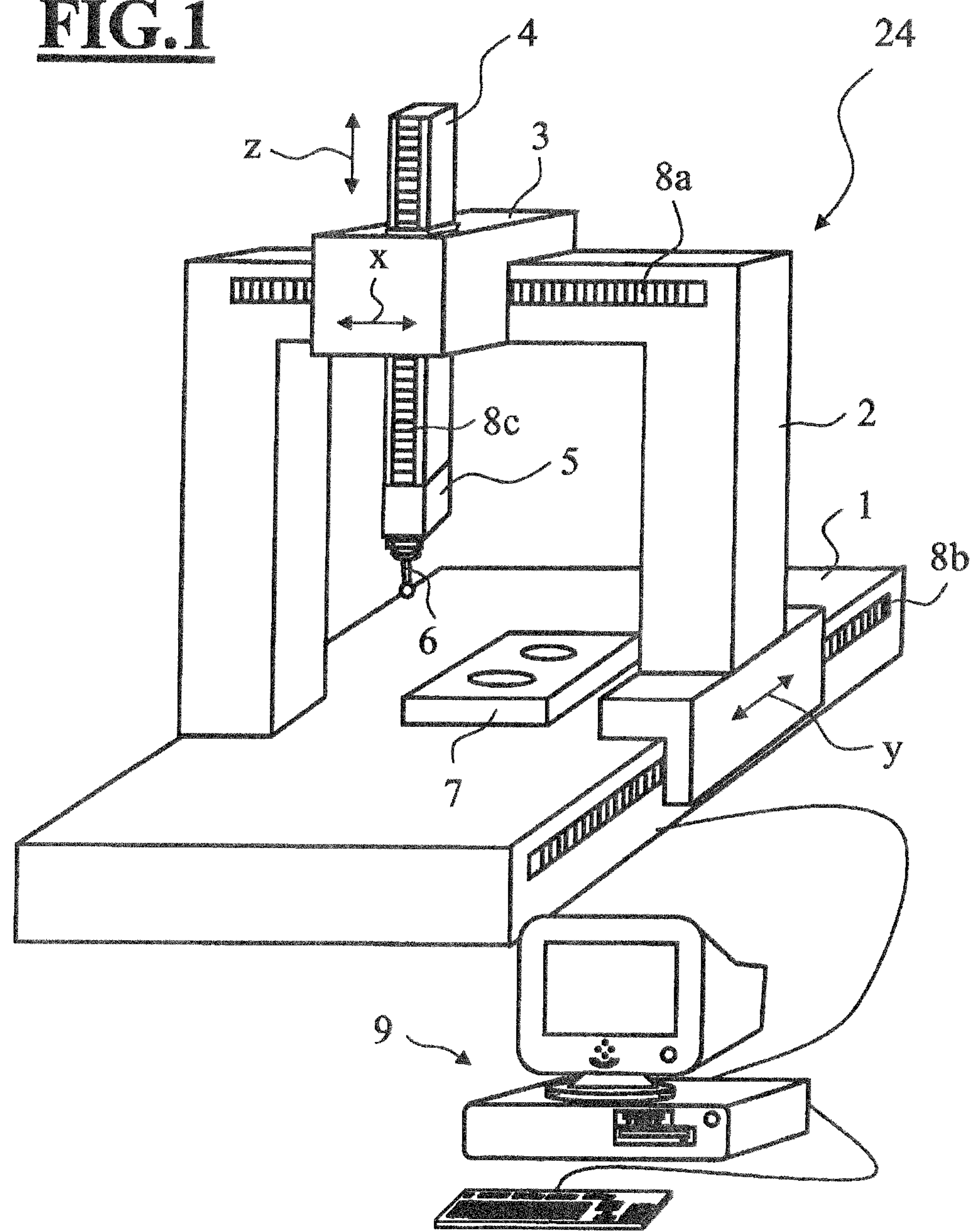
FIG. 1 shows a coordinate measuring machine with a portal configuration.

FIG. 1 shows a coordinate measuring machine 24 with a so-called portal configuration in a purely exemplary manner.

In coordinate metrology, bridge- or column-type coordinate measuring machines and multipoint measuring machines or articulated arm coordinate measuring machines are also conventional.

The coordinate measuring machine 24 has a stylus 6, which is fastened in a replaceable manner to a probe head 5 and which can be deflected in relation to the probe head 5 in the three coordinate directions x, y and z. The deflection of the stylus 6 in the three coordinate directions x, y and z is detected by way of three transducers situated in the probe head 5. The probe head 5 in turn can be moved in the three coordinate directions x, y and z. To this end, the portal mechanism has a measuring unit 2, which can be displaced in relation to the measurement table 1 in the coordinate direction denoted by the arrow y. The so-called measuring slider 3 is movably guided in the direction denoted by the arrow x along the crossbeam of the measuring unit 2 spanning the measurement table 1. The quill 4 is in turn movably guided on the measuring slider 3 in the vertical direction denoted by the arrow z such that the probe head 5 can be displaced in the three coordinate directions x, y and z by way of the portal mechanism. A workpiece is now measured in such a way that the stylus 6 probes the workpiece 7 to be measured at predetermined measurement points, wherein the deflection in terms of the three coordinate directions x, y and z of the stylus 6 in relation to the probe head 5 is measured in the probe head 5. Additionally, the current position of the probe head 5 is measured along the three coordinate directions x, y and z at the three incremental scales 8*a* to 8*c*, which are scanned by optical reader heads. In order to establish a measurement point, the scale measured values 8*a* to 8*c* are combined by calculation in terms of the correct components with the stylus deflections established by the transducers in the probe head 5 and a measurement point is generated herefrom.

Different styluses are usually required in order now to be able to measure complex workpieces with a complex geometry and the styluses are stored in a cartridge (not depicted here) and can be inserted in an automated manner by way of a changer apparatus at the probe head 5. The different styluses usually have one or more probe shafts, at the ends of which it is possible to fasten a probe body, such as, for example, a probe sphere or a cylinder. By way of example, it will be possible to measure a horizontal hole only using a horizontally aligned probe shaft, that is, using a so-called laterally arranged stylus 6, while it is possible to measure a vertical hole only using a vertically aligned probe shaft.

The measurement process and the drive means of the coordinate measuring machine are controlled and the measured values established in the process are recorded and evaluated by means of a control and evaluation unit 9, which, in an exemplary manner, is realized by a single computer in this embodiment. The control and evaluation unit 9 can additionally be connected to an operating console (not depicted here) by means of which the coordinate measuring machine can also be displaced manually in the coordinate directions x, y and z by way of operating lever and by means of which it is also possible to undertake other functions, such as, for example, a change of stylus or an operation of the measuring program.

Figure 2:
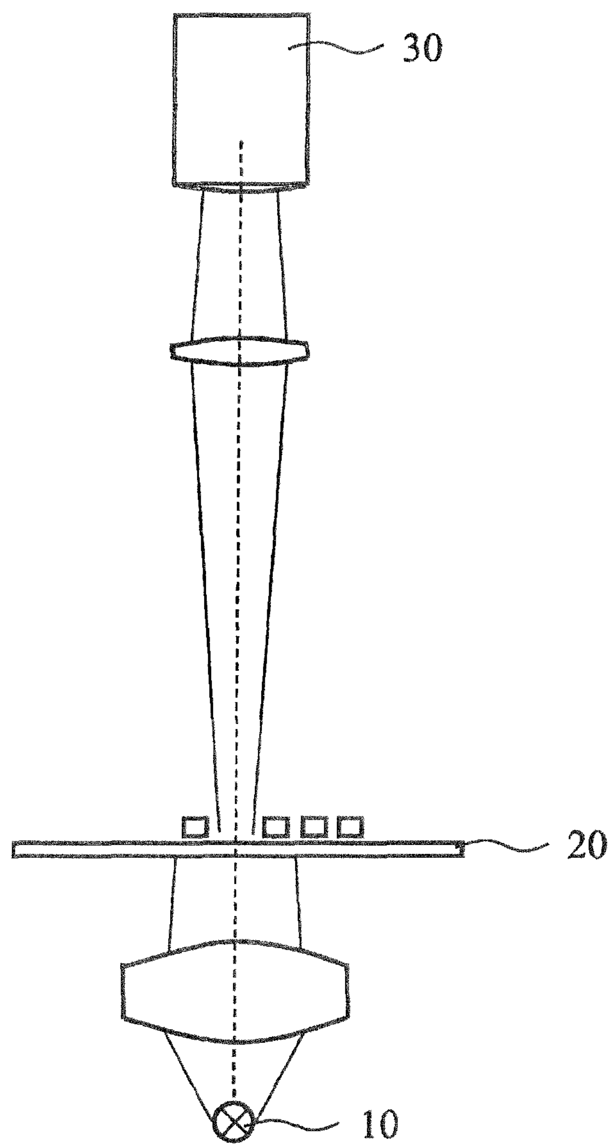
FIG. 2 shows a schematic of the transmitted-light illumination for optical image capturing.

As an alternative to a probe head 5, the coordinate measuring machine 24 in FIG. 1 can also be equipped with an optical measuring system in accordance with FIG. 2. This optical measuring system includes a CCD or CMOS sensor or another light-sensitive array for spatially resolved conversion of light into signals which are able to be stored and used in computers, a lens and an illumination system. With the aid of the coordinate measuring machine, the optical measuring system can be displaced in a targeted manner to the position of the workpiece to be measured. There, recordings of the workpiece are subsequently made with the aid of the CCD or CMOS sensor, the lens and the illumination system. By using image processing software for the recordings made and taking into consideration the scale measured values 8*a* to 8*c* of the coordinate measuring machine, the coordinates of the observed relevant structures are then output.

It is to be appreciated that the present invention can also be used for different types of coordinate measuring machines than the coordinate measuring machine 24 with a portal configuration shown in FIG. 1, in particular for bridge- or column-type coordinate measuring machines.

FIG. 2 shows by way of example an optical measuring system for coordinate measuring machines for recording images of a workpiece 20 using a CCD or CMOS camera of the prior art, wherein the workpiece 20 is illuminated using transmitted-light illumination with the aid of a light source 10.

The transmitted-light illumination according to FIG. 2 is frequently used for measuring outer edges, holes or breakthroughs in workpieces. Flat workpieces such as sheet-metal parts or the chrome structures used for initial measurement and calibration on glass can also be measured "through" the workpiece using the transmitted-light illumination according to FIG. 2 by way of illuminating from the rear of the workpiece. The transmitted-light illumination must be matched to the imaging beam path in particular when measuring outer edges. Depending on the type of construction of the transmitted-light illumination unit (for example, critical or Köhler illumination) in the prior art, a different opening angle (aperture) of the illumination light is produced, which must be matched to the opening angle of the lens that is used. In particular when using zoom lenses, the transmitted-light illumination unit should ensure corresponding matching of the illumination opening angle to the variable opening angle of the zoom lens. The transmitted-light illumination units of the prior art thus typically include complicated and variable condenser optics. On the other hand, simple and cost-effective light-emitting tables of the prior art do not permit the matching of the illumination angle at the light-emitting table field to the conditions of the lens. In particular the provision of collimated illumination light is not known in such simple light-emitting tables of the prior art.

Since typically only a small portion of the features of a workpiece is capable of being measured using transmitted-light illumination, additionally reflected-light illumination such as brightfield reflected-light illumination and darkfield reflected-light illumination is used in coordinate measuring machines of the prior art.

Figure 3:
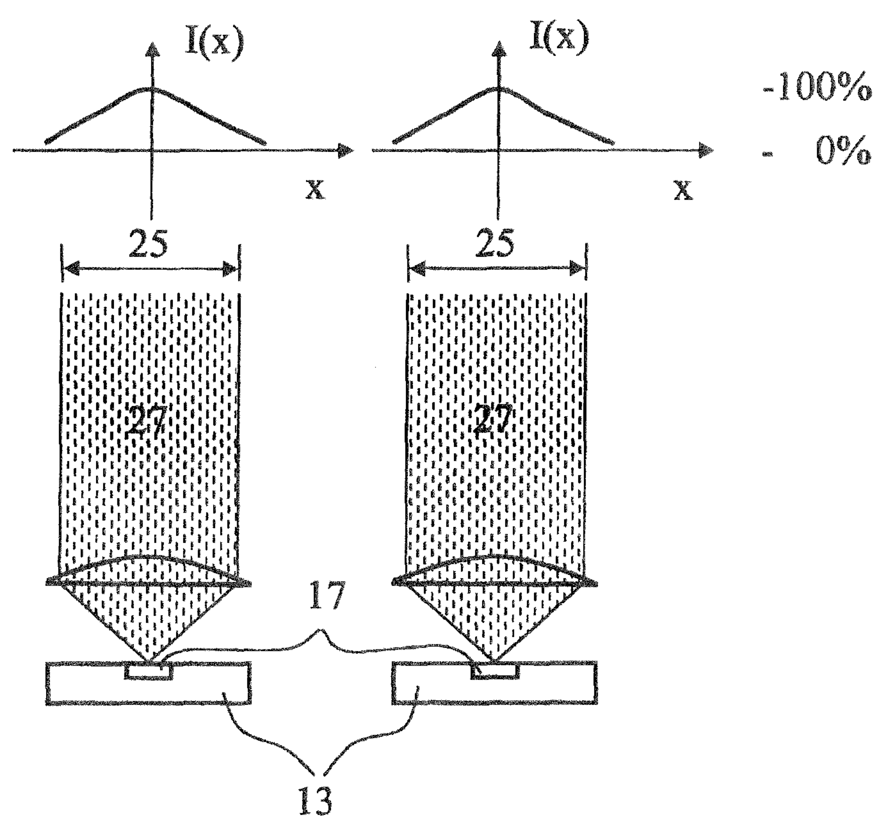
FIG. 3 shows a schematic of the light distribution in the case of a grid of LED light sources with collimation lens elements of the prior art.

FIG. 3 shows by way of example the spatial relationships of the light distribution in light-emitting tables of the prior art with reference to two adjacent LED light sources 13. It is clear that the actual light-emitting surface 17 of the LED 13 is much smaller than the total surface of the LED light source 13 and that the two LED light sources 13 are moreover spaced apart from each other. The spacing between the LED light sources 13 is a result of the space needed for electric supply and also, in high-power LED light sources, of the installation space required for heat dissipation. For the above-mentioned reasons it is therefore not possible on account of the use of LED light sources to produce a homogeneously light-emitting surface without having non-light-emitting intermediate spaces.

In the arrangement of LED light sources 13 according to FIG. 3, the illumination light is collimated by lens elements 29 being arranged above the light sources 13. It is possible by way of the lens elements 29 or correspondingly diffractively functioning optical elements or alternatively by way of corresponding reflectors, in which the light-emitting surface 17 of the LED light sources 13 is located in the focal point or within the caustics, to align the illumination light from the emission angle interval of the light sources 13 to be parallel and thus to collimate it. The resulting primary light channels 27 of the light-emitting table are shown in FIG. 3 in dashed form. The light channels 27 are here defined by the free passable regions 25, which are provided either by the optically free regions of the lens elements 29 or by the maximum extent of the light cones of the light sources 13, depending on which of these have a delimiting effect. In principle, it is possible with this approach, when additionally using immersion optics in connecting the lens elements 29 to the light sources 13, to increase the yield of collimated light to nearly 100% of the illumination light emitted by the light sources 13. However, the illumination light collimated by the lens elements 29 has, in a plane above the lens elements 29, strong inhomogeneities over the observed plane, as are represented schematically in FIG. 3. What can be seen is that no illumination light is present between the light channels 27 and that even within the light channels 27 the light is distributed highly inhomogeneously. The illumination light is highly concentrated near the centers of the light channels and thus near the light source axes which exit in the centers of the light-emitting surfaces 17. However, only a small amount of illumination light is present at the boundaries of the light channels 27. This is primarily due to the fact that LED light sources do not emit equal amounts of light in all spatial directions, but emit light in a targeted fashion in the region around the light source axis. Using collimation means such as a lens element 29, a diffractive optical element or a corresponding reflector, it is possible to align the light from an LED light source such that it is parallel, but not to simultaneously homogenize it even within the resulting light channel.

Another approach in light-emitting tables using LED light sources is to use diffuser plates or diffuser films instead of lens elements above the LED light sources in order to produce a homogeneously illuminated luminous field in the far field of the light sources. In the case of this approach, the light-emitting table field is indeed illuminated homogeneously, but the field emits light diffusely owing to scattering and thus nearly in all directions above the light-emitting table. A collimated beam path can thus not be obtained for the illumination light.

Consequently, in light-emitting tables of the prior art it is possible, using simple means, to cost-effectively set either only a homogeneous light-emitting table field or only a collimated illumination beam emerging from the light-emitting table field. Effecting both settings at the same time using cost-effective measures is not known in the prior art.

Figure 4:
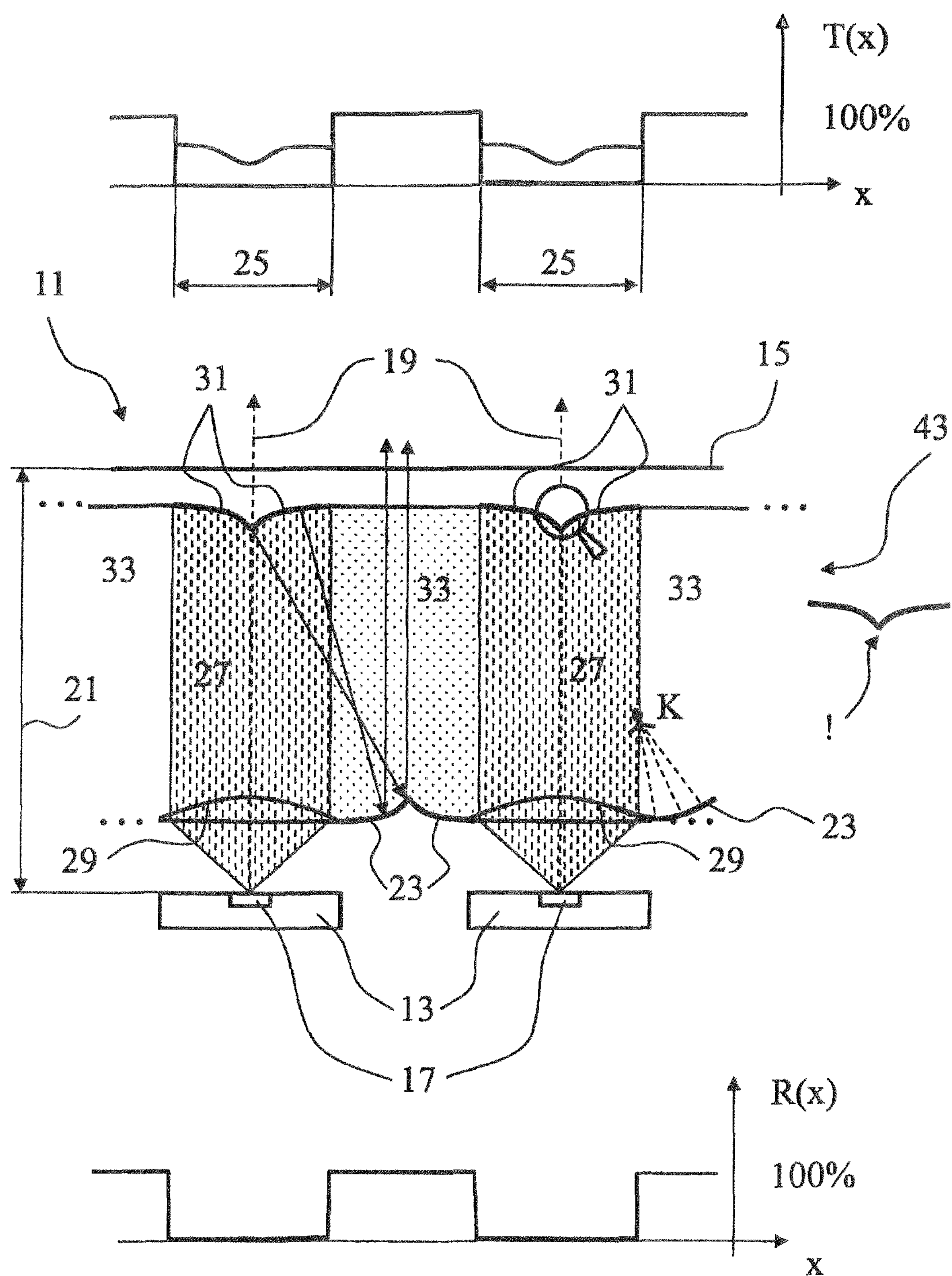
FIG. 4 shows a schematic of a first embodiment of a light-emitting table according to the invention.

FIG. 4 schematically shows a first embodiment of a light-emitting table 11 according to the invention, in which the represented embodiment includes an optically transparent carrier material 43 which is configured in one part. Here, the unipartite carrier material 43 of the light-emitting table 11 can be produced cost-effectively by way of plastic injection molding, pressing/thermoforming methods or cold or hot forming of plastics sheets.

FIG. 4 initially shows again the two LED light sources 13 and the beam path which is collimated by lens elements 29 above the light sources 13 in the form of primary light channels 27 according to the free passable regions 25 similar to FIG. 3. These primary light channels 27 are graphically represented by way of short dashes in FIG. 4 as in FIG. 3. The represented lens elements 29 can be produced cost-effectively after the plastics material of the unipartite carrier material 43 has been impressed in the plastic injection molding or cold or hot forming method, for example, using droplet deposition of the lens-element material in the impressed depressions in the plastics material.

The first embodiment of the light-emitting table 11 according to the invention, which is represented in FIG. 4, now differs from a light-emitting table of the prior art in accordance with FIG. 3 in that the light-emitting centers 17 of the light sources 13 represent the starting points of light source axes 19 which perpendicularly intersect the field 15 to be illuminated, and wherein the light-emitting centers 17 of the light sources 13 on one side and the field 15 to be illuminated on the other side delimit an intermediate space 21 in the interior of the light-emitting table 11, wherein located between the light source axes 19 within the intermediate space are curved and mirrored surfaces 23, the focal points or caustics K of which are located within the intermediate space 21 between the curved and mirrored surfaces 23 and the field 15 to be illuminated.

Owing to the curved and mirrored surfaces 23 between the light source axes 19, which, due to the stated position of the focal points or caustics K, are aligned with the field 15 to be illuminated, it is possible to fill the otherwise unused shadow region 33 between the light sources 13 with illumination light and at the same time maintain the collimation of the illumination light. Owing to the curved and mirrored surfaces 23 it is thus possible both to improve the homogeneity of the light-emitting table 11 and to ensure collimation of the illumination light. Within the context of this application, the regions 33 which are supplied with illumination light by way of the mirrored surfaces 23 are referred to as secondary light channels 33. FIG. 4 shows the central secondary light channel 33 in dotted form to clarify the guidance of the light.

In order to supply the secondary light channels 33, the curved and mirrored surfaces 23 have surface shapes, the local curvatures of which are configured such that visible light that is incident on the field of the light-emitting table parallel to the light source axes and counter to the illumination direction of the light-emitting table collects, owing to the curved and mirrored surfaces, in focal points or caustics K above the light sources and above the curved and mirrored surfaces in the intermediate space between the light sources and the field of the light-emitting table. In other words, neither the light sources 13 nor the light-emitting centers 17 of the light sources 13 are located in the focal points or within the caustics K of the curved and mirrored surfaces 23 of the light-emitting table 11 according to the invention viewed under normal incidence of light on the light-emitting table field from infinity. The position of the caustics K can be seen in FIG. 4 by way of a caustic K (illustrated for a mirror 23) in which the beams (represented in dashed form) collect for normal incidence of light from infinity.

The light sources 13 represented in FIG. 4 are arranged parallel in a regular first pattern having spacings of 0.2 cm to 4 cm, and the curved and mirrored surfaces 23 are arranged in a second pattern, corresponding to the first pattern, with a lateral offset to the light sources 13 or to the light source axes 19 in a plane that is perpendicular to the drawing plane, with the result that next to the curved and mirrored surfaces 23, free regions 25 through which illumination light is able to pass are located around the light source axes 19. This type of construction of the light-emitting table 11 permits the illumination light from the light sources 13 to be incident on the field 15 of the light-emitting table 11 without considerable losses along first, so-called primary light channels 27 and to cause here illumination of the field 15.

In the light-emitting table 11 represented in FIG. 4, light-deflecting and/or light-refracting and/or light-diffracting means 29, which align the illumination light within the primary light channel 27 parallel to the light source axis 19 with a parallelism of better than 2°, are located within the primary light channels 27 of the light-emitting table 11, wherein the means 29 drawn in FIG. 4 are made up of lens elements 29. The means 29 could likewise be made up of the group: curved mirrors, parabolic mirrors, hyperboloidal mirrors, ellipsoidal mirrors, lens elements, Fresnel lens elements, cylindrical lens elements, microlens elements, honeycomb condensers, diffractive optical elements.

The collimation means 29 make it possible for the illumination light from the light sources 13 to be aligned parallel in the primary light channels 27. As a result, the illumination light is incident on the field 15 of the light-emitting table 11 from a nearly normal direction. As a result, a larger variation of illumination angles at the field points of the light-emitting table within the primary light channels 27 is avoided, especially since the use of diffusing optical elements for homogenization in the primary light channels 27 in the light-emitting table 11 according to the invention is entirely dispensed with.

In the light-emitting table 11 represented in FIG. 4, further curved and partially mirrored surfaces 31 which reflect a proportion of illumination light out of the primary light channels 27 toward the curved and mirrored surfaces 23 at angles of up to 50° with respect to the light source axes 19 are located in the primary light channels 27 of the light-emitting table 11, which are defined by the free regions 25 around the light source axes 19, between the curved and mirrored surfaces 23 and the field 15 of the light-emitting table 11. Owing to these further curved and partially mirrored surfaces 31 within the primary light channels 27, a proportion of illumination light is coupled out of the primary light channels 27 and used for supplying the secondary light channels 33 which are formed or defined by the curved and mirrored surfaces 23 next to the light source axes 19.

Here, the light sources 13 of the light-emitting table 11 in FIG. 4 are provided by way of example by what are known as LEDs or OLEDs, and the local curvatures of the curved and mirrored surfaces 23 and the local curvatures of the further curved and partially mirrored surfaces 31 are configured with respect to one another such that the illumination light, which travels within the primary light channels 27 near the light source axis 19 and is reflected by the surfaces 31 or 23, subsequently travels within the secondary light channels 33, which are defined by the curved and mirrored surfaces 23, remote from the light source axis, and vice versa.

What is achieved with this type of redistribution of illumination light in the secondary light channels 33 is that light which previously traveled within the primary light channel 27 near the light source axis 19 travels, after it has been coupled out, in the respective secondary light channel 33 remote from the light source axis. This type of redistribution makes sense in particular for homogenizing the field of light-emitting tables 11 with LED or OLED light sources 13, since these light sources 13 have an emission characteristic with which most of the light is emitted closely around the light source axis 19. In addition, this also counters the geometric effect that the surface regions of the secondary light channels 33, which are to be supplied with light, are, in terms of their surface area, a function of the square of the distance from the respective light source axis 19.

In this case, the reflectivity properties along the partially mirrored surfaces 31 of the light-emitting table 11 of FIG. 4 are additionally configured such that higher reflectivity values of the partially mirrored surfaces 31 are present around the light source axes 19 than at the boundaries of the partially mirrored surfaces 31, with the result that proportionally more illumination light is reflected out of the primary light channels 27 if this illumination light in the primary light channels 27 travels near the light source axis 19 before it is reflected out. This stated measure does not only serve for homogenizing the illumination light from LED or OLED light sources 13 within the primary light channels 27 of the light-emitting table 11, compared to light-emitting tables of the prior art in accordance with FIG. 3, by reducing here the illumination light in the primary light channels by way of increased outward reflection, where too much light for homogenization is already present anyway, but also for supplying most of the decoupled light to the boundaries of the secondary light channels. The transmittance curve of the coating on the upper side of the unipartite carrier material 43 is represented in the top part of FIG. 4. If a negligible absorption in the coating is assumed, the inverse of the represented transmittance curve represents the reflectance curve of the coating on the upper side. What is clear from the represented curve is that the lowest transmittance and thus highest reflectance occurs in the center around the light source axis 19 of a primary light channel 27. The profile within a primary light channel 27 of the transmittance curve is here selected such that the natural illumination intensity profile of a collimated LED light source, represented in FIG. 3, is homogenized, that is, set to a constant value within the primary light channel. Owing to the highest reflectance being in the center of a primary light channel 27 around the light source axis 19, it is furthermore additionally ensured that the secondary light channels 33 are supplied with a sufficient amount of light. In contrast to the transmittance or reflectance profile of the curved and partially mirrored surfaces 31, the reflectance over the curved and mirrored surfaces 23 is nearly constant with almost 100% reflectance. The corresponding profile of the reflectance for the lower side of the carrier material 43 can be seen in the bottom part of FIG. 4.

In the embodiment of the light-emitting table 11 according to the invention represented in FIG. 4, the local curvatures of the curved and mirrored surfaces 23 and also the local curvatures of the further curved and partially mirrored surfaces 31 are configured with respect to one another such that the parallelism of the illumination light, which was originally achieved using the light-deflecting and/or light-refracting and/or light-diffracting means 29 in the primary light channels 27, with respect to the light source axis 19 of better than 2° is maintained in the further passage in the secondary light channels 33 after the proportional outward reflection by way of the further curved and partially mirrored surfaces 31 and the deflection by way of the curved and mirrored surfaces 23. What is achieved as a result is that parallelism of the illumination light in the primary light channels 27, which is attained using the collimation means 29, is not destroyed again through outward reflection and deflection into the secondary light channels 33.

However, the embodiment of FIG. 4 serving for explaining the invention also has disadvantages relating to production technology. The discontinuity in the upper surface of the carrier material 43, which is enlarged in FIG. 4 by way of a magnifying glass and is marked with an exclamation point, must therefore be positioned very precisely on the light source axis 19 of the respectively associated LED light source 13, since otherwise too much light is distributed either to the left or to the right. This would prevent the desired homogenization, especially since the discontinuity is situated at the place of highest intensity in the beam path within the primary light channel 27 and therefore provides the greatest lever for a right-left asymmetry. However, such exact positioning of the discontinuity is very difficult to implement in terms of production technology, since both the inaccuracies of the LED position and the inaccuracies of the production process must be taken into consideration in the production of the carrier element 43. Moreover, the illumination light in the primary light channel 27, which passes through the curved and partially mirrored surfaces 31 near the discontinuity, is also refracted by the surfaces 31 which are highly inclined in the area around the discontinuity, with the result that the previously achieved collimation there is lost again.

Figure 5:
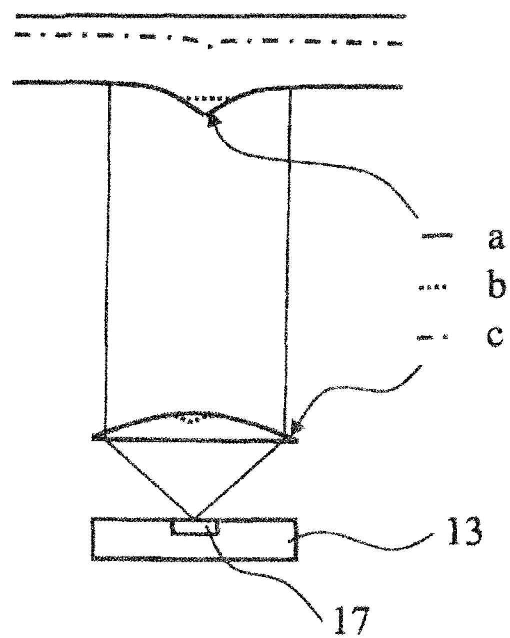
FIG. 5 shows a schematic of a second embodiment of the light-emitting table according to the invention.

FIG. 5 now schematically shows various possibilities for addressing the problems caused by the discontinuity in the upper side of the carrier material 43. The starting situation in FIG. 4 with the discontinuity in the upper side of the carrier material 43 is here represented in FIG. 5 by way of the solid line of option a. First, there is the possibility of replacing the discontinuity in the upper side (option a) with a continuously differentiable profile and of providing at the same time an allowance in the surface form of the collimation lens element 29. This is drawn in dotted form in FIG. 5 as option b. This does significantly reduce the production and positioning problems of the discontinuity in the upper side, but increases the production outlay for the now at least aspherical lens element 29. Alternatively to the allowance in the surface form of the lens element 29 and the associated production outlay, it is however possible to deposit or add further material of the carrier material 43 on the upper side, which itself has a reduced discontinuity in its profile. This is demonstrated in FIG. 5 as the dashed-dotted option c. However, it is far more appealing to deposit or add further material having a lower optical density than the carrier material 43 on the latter. With suitable selection of the optical densities of carrier material 43 and the further material, it is even possible to entirely avoid the further reduced discontinuity on the upper side of the further material, which results overall in a carrier material 43 of at least two layers of different material, the surfaces of which are planar. This situation is represented in FIG. 5 by way of the solid and straight line above option c.

Figure 6:
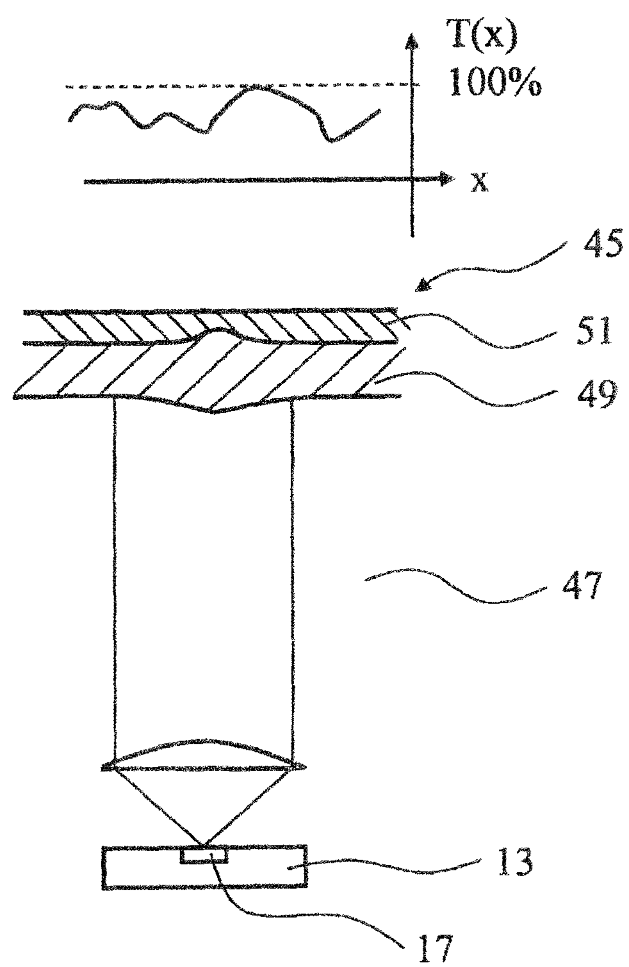
FIG. 6 shows a schematic of a third embodiment.

FIG. 6 now shows by way of example a detail of one embodiment of the light-emitting table 11 according to the invention, including a unipartite carrier material 43 consisting of three layers 47, 49 and 51 of different materials having different optical densities. What can be seen is that the discontinuity which was discussed in connection with FIG. 4 has been replaced by two continuously differentiable places, arranged one above the other, in the boundary surfaces between the material 47 and the material 49 and between the material 49 and the material 51. This illustrated embodiment permits a planar surface of the unipartite carrier material 43, with the result that, for example, what is known as a neutral density filter (ND filter) 45 for correcting local inhomogeneities can be deposited or placed on the upper side. In particular short-wave transmittance modulations, as are illustrated in the upper part of FIG. 6, can be eliminated with the aid of such a filter. Furthermore, such filters 45 can also be deposited or placed subsequently, with the result that final correction of the light-emitting table 11 is made possible with the aid of the ND filter 45 after its measurement for transfer into an acceptance specification. Also conceivable would be a prescription manufacture of the ND filter 45, with the result that particular customer-specific illumination intensity profiles can be imparted on the light-emitting table 11.

However, the planar surface of the embodiment represented in FIG. 6 also permits placement or deposition of further functional layers. Conceivable as such would be polarizers, short pass filters, long pass filters, bandpass filters or what are known as Vikuiti filters. Moreover, liquid-crystal optics for example for targeted change of the emission angles or pixel arrays for pixel-resolved variation of the transmittance can also be placed immediately above the planar surface.

Figure 7:
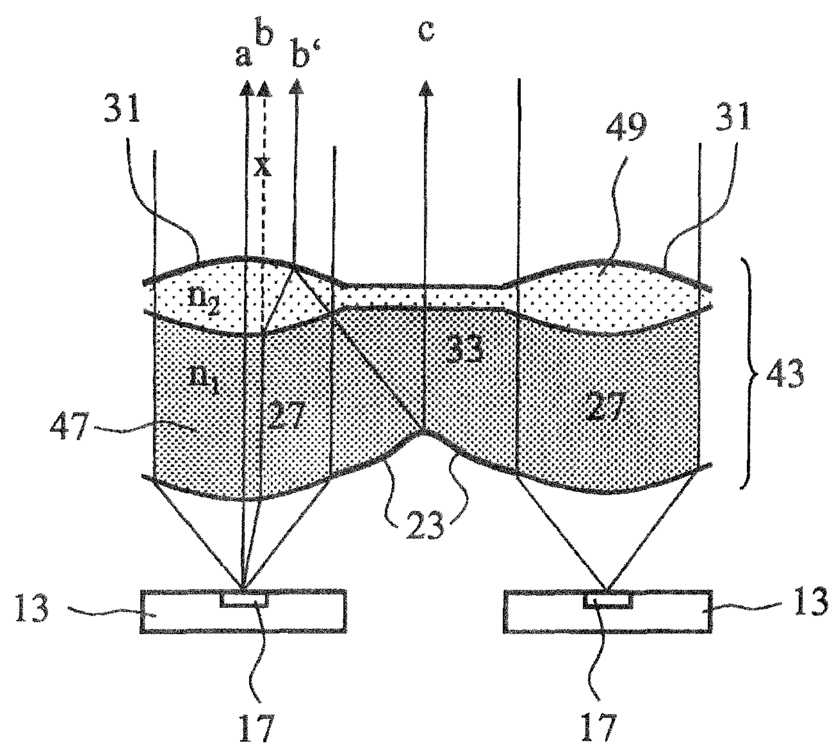
FIG. 7 shows a schematic of a fourth embodiment.

FIG. 7 schematically represents a further embodiment of the light-emitting table 11 according to the invention, including a unipartite carrier material 43 having two layers (47, 49) of different materials having the optical densities n1 and n2, in which all relevant and previously described optical elements and surfaces of the light-emitting table 11 according to the invention are integrated. To illustrate the mode of function, the beams a, b, b' and c are drawn in FIG. 7. The beam a emitted by the light-emitting surface 17 along the light source axis 19 of the LED light source 13 passes through the unipartite carrier material 43 without being deflected and nearly without being attenuated. The beam b, which merely has a slight lateral offset with respect to beam a, is refracted at the curved boundary surface between materials 47 and 49 and thus reaches the field of the light-emitting table not by way of a straight path. The beam b is therefore marked, in its further profile, in FIG. 7 by way of an x as non-existent. The refracted beam b, on the other hand, in its further path through the material 49, is ultimately incident on the curved upper side of the material 49, on which a partially mirrored coating is situated, which decomposes the beam b proportionally into a transmitting beam b' and a reflected beam c. The reflected beam c, in turn, is reflected by a reflective coating on the curved underside of the material 47 back in the direction of the light-emitting table field. The unipartite carrier material 43 which is represented in FIG. 7 can now be produced cost-effectively and simply in terms of production technology by way of cold/hot forming or by way of pressing/thermoforming of sheets of the materials 47 and 49 or be deposited by corresponding injection molding methods, wherein it is also possible for only one of the materials 47 and 49 to be deposited on the respectively other material (47, 49).

In particular, the curved and mirrored surfaces 23, which are in contact with one another, of the embodiment of the light-emitting table according to the invention illustrated in FIG. 7 can be formed on the unipartite carrier material 43 by way of a pressing/thermoforming method or by cold/hot forming, wherein the surface coating for rendering the curved and mirrored surfaces 23 reflective is done by way of a method which includes at least one process step and/or one method step from the group: varnishing, vapor deposition, sputtering, separation from a chemical solution, grayscale lithography and subtractive methods for locally varying removal of a previously applied surface coating.

With particular preference, the unipartite carrier material 43 of the embodiment illustrated in FIG. 7 of the light-emitting table 11 according to the invention likewise includes the light-deflecting and/or the light-refracting and/or the light-diffracting means 29 of the light-emitting table 11, wherein the means 29 are formed by a pressing/thermoforming method and/or by cold/hot forming and/or by a surface coating, wherein the surface coating includes at least one process step and/or method step from the group: varnishing, vapor deposition, sputtering, separation from a chemical solution, grayscale lithography and subtractive methods for locally varying removal of a previously applied surface coating.

Moreover, the further curved and partially mirrored surfaces 31 of the light-emitting table 11 according to the invention of the embodiment illustrated in FIG. 7 can likewise be formed on the unipartite carrier material 43 by way of a pressing/thermoforming method or by cold/hot forming, wherein the surface coating for rendering the further curved and partially mirrored surfaces 31 reflective is done by way of a method which includes at least one process step and/or one method step from the group: varnishing, vapor deposition, sputtering, separation from a chemical solution, grayscale lithography and subtractive methods for locally varying removal of a previously applied surface coating.

The embodiment, illustrated in FIG. 7, of the light-emitting table 11 according to the invention, corresponding to the embodiment in accordance with FIG. 6, can furthermore have an ND filter 45 for reducing the variation of the illumination intensity over the field 15 to be illuminated. In this case, the ND filter 45 can be formed on the unipartite carrier material 43 and produced by way of surface coating, wherein the surface coating includes at least one process step and/or one method step from the group: varnishing, vapor deposition, sputtering, separation from a chemical solution, grayscale lithography and subtractive methods for locally varying removal of a previously applied surface coating.

The embodiment, illustrated in FIG. 7, of a light-emitting table 11 according to the invention is characterized in particular by the fact that the unipartite carrier material 43 is assembled from at least two layers (47, 49) of different materials having different optical densities (n1, n2), and the layers (47, 49) have locally varying, different geometric thicknesses along the lateral extent of the carrier material 43 perpendicular to the light source axes 19.

Figure 8:
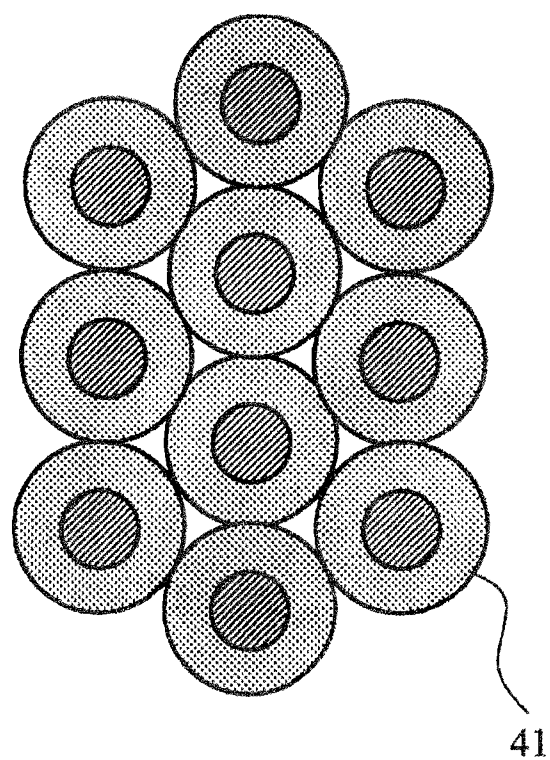
FIG. 8 shows a schematic of a possible arrangement of an embodiment according to the invention in plan view.
Figure 9:
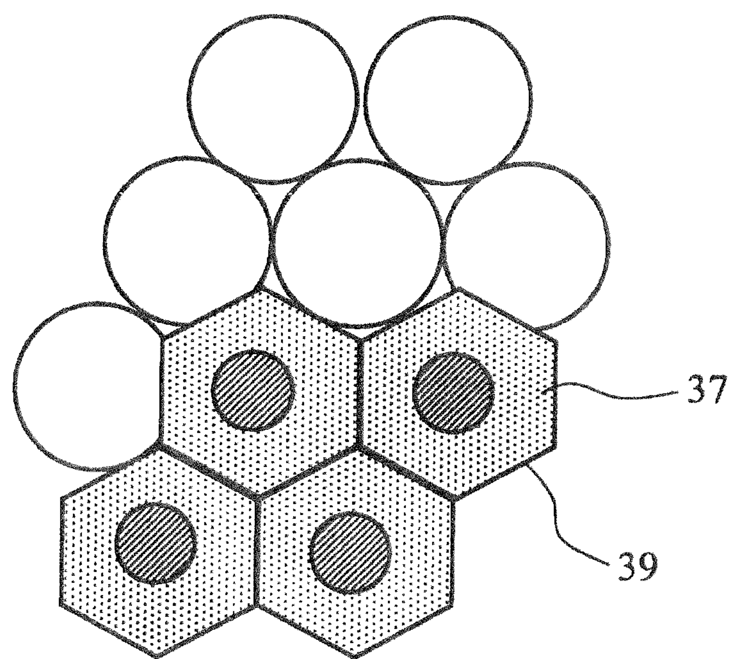
FIG. 9 shows a schematic of a further possible arrangement of an embodiment according to the invention in plan view; and, FIG. 10 shows a perspective schematic of a detail of a variant of the further possible embodiment of FIG. 9.

FIG. 8 and FIG. 9 show, in plan view, possible embodiments of a light-emitting table 11 according to the invention, wherein the passable free regions 25 around the light source axes 19 are configured to be circular or elliptical, and the curved and mirrored surfaces 23 represent contiguous, continuously differentiable surface regions 37, wherein the mentioned surface regions 37 have honeycomb-type 39 or circular or elliptical 41 boundaries and are at least partially in contact with one another at the boundaries (39, 41). As a result, optimal covering of the light-emitting table 11 with secondary light channels 33 around the primary light channels 27 is ensured.

Figure 10:
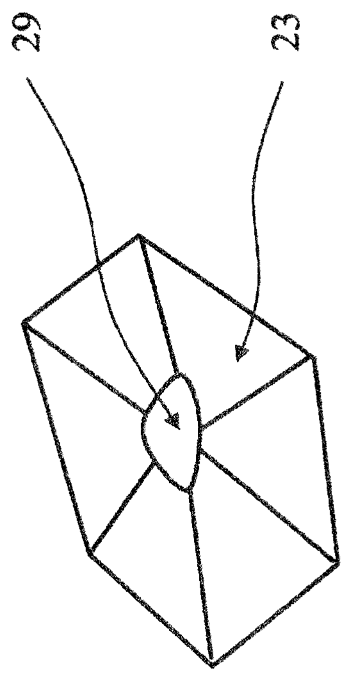

The embodiments illustrated in FIGS. 8 and 9 in plan view can correspond to embodiments discussed in connection with FIGS. 4 to 7, but they can also correspond to other embodiments, in which the curved and mirrored surfaces 23 are formed similar to the plastics bottom of a box of chocolates, which in its center in the passable free regions 25 hold collimation lens elements 29 corresponding to chocolates in a box of chocolates. Such an embodiment is represented in more detail in FIG. 10. In this embodiment, the curved and mirrored surfaces 23 are no longer of rotation-symmetrical design but follow the honeycomb-type boundary structure. Alternatively to holding collimation lens elements 29 by way of the curved and mirrored surfaces 23, the curved and mirrored surfaces 23 can have, for example, depressions, produced by way of a thermoforming method, in the form of rotating parabolic/hyperbolic or ellipsoidal surfaces within the passable free regions 25, in the cut-free focal points of which the LED light sources can be positioned. It would thus be possible, similar to a plastics bottom of a box of chocolates, to produce the primary structure of the light-emitting table 11 according to the invention with the curved and mirrored surfaces 23 in a cost-effective manner.

The discussed embodiments of the light-emitting table 11 according to the invention ensure variation of the illumination intensity over the field 15 of the light-emitting table 11 of less than 3% of the average illumination intensity of the field 15, and a variation of the illumination angles at a point of the field (15) of less than 2°. In this case, the light-emitting tables 11 according to the invention can be limited to a maximum installation height of 10 cm owing to the use of the curved and mirrored surfaces 23. The light-emitting tables according to the invention are particularly suitable for use in metrology owing to the good homogeneity and the low variation in the illumination angle. It is possible especially by way of the achievable small installation height to equip or retrofit coordinate measuring machines 24 for capturing the coordinates of a workpiece 7 according to FIG. 1 with such a light-emitting table 11 according to the invention.

It is understood that the foregoing description is that of the preferred embodiments of the invention and that various changes and modifications may be made thereto without departing from the spirit and scope of the invention as defined in the appended claims.

What is claimed is:

1. A light-emitting table configured for use in metrology, the light-emitting table comprising:

a plurality of light sources each having a light-emitting center representing a starting point of a light source axis and configured to output illumination light;

the light-emitting table defining a field to be illuminated and a table interior;

said light source axes perpendicularly intersecting said field to be illuminated;

said light-emitting centers of said light sources and said field to be illuminated conjointly defining an intermediate space therebetween in said table interior;

a plurality of first curved and mirrored surfaces disposed between each two mutually adjacent ones of said light source axes within said intermediate space;

said first curved and mirrored surfaces defining respective focal points or caustics (K) disposed within said intermediate space between said curved and mirrored surfaces and said field to be illuminated;

said light sources being arranged in parallel in a regular first pattern with each two mutually adjacent ones thereof conjointly defining a spacing therebetween lying in a range of 0.2 cm to 4 cm;

said first curved and mirrored surfaces being arranged in a second pattern corresponding to said first pattern with a lateral offset to said light sources and said light source axes so as to define free regions adjacent said first curved and mirrored surfaces through which the illumination light can pass to be disposed around said light source axes;

said free regions around said light sources defining respective primary light channels along corresponding ones of said light source axes starting at corresponding ones of said light sources;

a plurality of second curved and mirrored surfaces each configured to be partially mirrored and to reflect a respective proportion of said illumination light out of said primary light channels toward a corresponding one of said first curved and mirrored surfaces at angles up to 50° with respect to the corresponding one of said light source axes; and, said second curved and mirrored surfaces being disposed in said primary light channels between said first curved and mirrored surfaces and said field to be illuminated.

2. The light-emitting table of claim 1 further comprising:

at least one of light-deflecting means, light-refracting means and light-diffracting means disposed in corresponding ones of said primary light channels and configured to align said illumination light within said primary channels parallel to said light source axes with a parallelism of better than 2°;

said primary light channels extending along corresponding ones of said light source axes and having an expansion in a plane perpendicular to said light source axes through said free regions; and, said at least one of light-deflecting means, light-refracting means and light-defracting means being formed from a group including curved mirrors, parabolic mirrors, ellipsoidal mirrors, lens elements, fresnel lens elements, cylindrical lens elements, microlens elements, honeycomb condensers and diffractive optical elements.

3. The light-emitting table of claim 1, wherein:

said light sources are provided in the form of at least one of LEDs and OLEDs;

said first curved and mirrored surfaces define first local curvatures;

said second curved and mirrored surfaces define second local curvatures;

said first curved and mirrored surfaces are configured to define secondary light channels; and, said first local curvatures and said second local curvatures are configured with respect to each other so as to cause said illumination light, which travels near said light source axes and is reflected by said first and said second curved and mirrored surfaces, to subsequently travel within said secondary light channels remote from said light source axes and be redirected.

4. The light-emitting table of claim 3, wherein:

said illumination light travels along said light source axis in such a manner that proportionally more of said illumination light travels close to said light source axis than elsewhere in said primary light channel;

said second curved and mirrored surfaces define edges thereof; and, said second curved and mirrored surfaces are further configured such that higher reflectivity values of said second curved and mirrored surfaces are disposed around said light source axes than at said edges thereof so as to cause said illumination light to be reflected out of said primary light channel from close to said light source axis.

5. The light emitting table of claim 3 further comprising:

at least one of light-deflecting means, light-refracting means and light-diffracting means disposed in said primary light channels and configured to align said illumination light within said primary channels parallel to said light source axes with a parallelism of better than 2°;

said first curved and mirrored surfaces defining first local curvatures;

said second curved and mirrored surfaces defining second local curvatures; and, said first and said second local curvatures being configured with respect to each other so as to cause said parallelism of better than 2° of said illumination light with respect to said light source axes initially achieved using said at least one of said light-deflecting means, said light-refracting means and said light-diffracting means in said primary channels to be retained in a further course in said secondary channels after said proportion of said illumination light is reflected out by said second curved and mirrored surfaces and is redirected by said first curved and mirrored surfaces.

6. The light-emitting table of claim 1, wherein:

said field to be illuminated has a variation in illumination intensity of less than 3% of an average illumination intensity of said field to be illuminated and a variation of an illumination angle at a point of said field to be illuminated is less than 2°; and, the light-emitting table has a maximum installation height of 10 cm.

7. The light emitting table of claim 1, wherein:

said first curved and mirrored surfaces are configured to define said free regions around said light source axes to have a circular or an elliptical shape;

said first curved and mirrored surfaces define interconnected, continuously differentiable surface regions;

said surface regions have at least one of honeycomb-like, circular and elliptical edges; and, said edges of mutually adjacent ones of said surface regions at least partially abut each other.

8. The light-emitting table of claim 7, wherein:

said first curved and mirrored surfaces, which abut each other, are formed on a one-piece carrier material via at least one of a pressing/thermoforming method, cold forming/hot forming, and plastic injection molding; and, said first curved and mirrored surfaces have a surface coating configured for reflection which is achieved via a method including at least a method step selected from a group including varnishing, vapor depositing, sputtering, separating from a chemical solution, grayscale lithography and subtractive methods for locally varying removal of a previously applied surface coating.

9. The light-emitting table of claim 8, further comprising:

at least one of light-deflecting means, light-refracting means and light-diffracting means disposed in said primary light channels and configured to align said illumination light within said primary channels parallel to said light source axes with a parallelism of better than 2°;

said one-piece carrier material also including said at least one of said light-deflecting means, said light-refracting means and said light-diffracting means; and, said at least one of said light-deflecting means, said light-refracting means and said light-diffracting means being formed via at least one of a pressing/thermoforming method, cold forming/hot forming, plastic injection molding, and surface coating, wherein said surface coating includes at least one method step from a group including varnishing, vapor depositing, sputtering, separating from a chemical solution, grayscale lithography and locally varying removal of a previously applied surface coating via subtractive methods.

10. The light-emitting table of claim 8, wherein:

said second curved and mirrored surfaces are also formed on said one-piece carrier material via at least one of a pressing/thermoforming method, plastic injection molding, and cold forming/hot forming; and, said second curved and mirrored surfaces each having a second surface coating configured for reflecting which is achieved via a method including at least a method step selected from a group including varnishing, vapor depositing, sputtering, separating from a chemical solution, grayscale lithography and subtractive methods for locally varying removal of a previously applied surface coating.

11. The light-emitting table of claim 1 further comprising an ND-filter configured to reduce a variation in light intensity over said field to be illuminated.

12. The light-emitting table of claim 8 further comprising:

an ND-filter formed on said one-piece carrier material and generated via a surface coating achieved via a method including at least a method step selected from a group including varnishing, vapor depositing, sputtering, separating from a chemical solution, grayscale lithography and subtractive methods for locally varying removal of a previously applied surface coating.

13. The light-emitting table of claim 8, wherein:

said one-piece carrier material includes at least two layers of different materials having different optical densities (n1, n2);

said one-piece carrier material defines a lateral expansion thereof perpendicular to said light source axes; and, said at least two layers have locally varying, different geometric thicknesses along said lateral expansion of said one-piece carrier material.

14. A coordinate measuring apparatus for determining coordinates of a workpiece, the coordinate measuring apparatus comprising:

an optical sensor;

a light-emitting table configured to illuminate the workpiece during a measurement of the coordinates of the workpiece via said optical sensor;

said light emitting table including a plurality of light sources each having a light-emitting center representing a starting point of a light source axis and configured to output illumination light;

said light-emitting table defining a field to be illuminated and a table interior;

said light source axes perpendicularly intersecting said field to be illuminated;

said light-emitting centers of said light sources and said field to be illuminated conjointly defining an intermediate space therebetween in said table interior;

said light-emitting table further including a plurality of first curved and mirrored surfaces disposed between each two mutually adjacent ones of said light source axes within said intermediate space;

said first curved and mirrored surfaces defining respective focal points or caustics (K) disposed within said intermediate space between said curved and mirrored surfaces and said field to be illuminated;

said light sources being arranged in parallel in a regular first pattern with each two mutually adjacent ones thereof conjointly defining a spacing therebetween lying in a range of 0.2 cm to 4 cm;

said first curved and mirrored surfaces being arranged in a second pattern corresponding to said first pattern with a lateral offset to said light sources and said light source axes so as to define free regions adjacent said first curved and mirrored surfaces through which the illumination light can pass to be disposed around said light source axes;

said free regions around said light sources defining respective primary light channels along corresponding ones of said light source axes starting at corresponding ones of said light sources;

said light-emitting table further including a plurality of second curved and mirrored surfaces configured to be partially mirrored and to reflect a respective proportion of said illumination light out of said primary light channels toward a corresponding one of said first curved and mirrored surfaces at angles up to 50° with respect to the corresponding one of said light source axes; and, said second curved and mirrored surfaces being disposed in said primary light channels between said first curved and mirrored surfaces and said field to be illuminated.

* * * * *

UNITED STATES PATENT AND TRADEMARK OFFICE

CERTIFICATE OF CORRECTION

PATENT NO. : 9,846,026 B2
APPLICATION NO. : 15/277254
DATED : December 19, 2017
INVENTOR(S) : Nils Haverkamp It is certified that error appears in the above-identified patent and that said Letters Patent is hereby corrected as shown below:

In the Claims

In Column 17:
Line 23: delete "light-defracting" and substitute -- light-diffracting -- therefor.

Signed and Sealed this
Third Day of April, 2018

Andrei Iancu
*Director of the United States Patent and Trademark Office*